United States Patent [19]

Linder et al.

[11] 4,413,999
[45] Nov. 8, 1983

[54] AMIDOXIME DERIVATIVES, PROCESSES FOR THE PREPARATION

[75] Inventors: Charles Linder, Rehovot; Gershon Aviv, Tel Aviv, both of Israel

[73] Assignee: Research Products Rehovot Ltd., Rehovot, Israel

[21] Appl. No.: 355,260

[22] Filed: Mar. 5, 1982

[30] Foreign Application Priority Data

Mar. 17, 1981 [IL] Israel ......................................... 62389

[51] Int. Cl.$^3$ ............................................. C08F 8/30
[52] U.S. Cl. .................................... 8/540; 544/312; 544/316; 525/149; 544/319; 544/320; 525/154; 544/337; 544/354; 525/157; 544/406; 544/407; 525/351; 546/141; 546/198; 525/359.2; 548/157; 548/167; 525/61; 548/221; 544/317; 528/423; 544/321; 544/405; 536/1.1; 544/408; 548/111; 536/31; 548/220; 544/194; 544/195; 544/182; 544/212; 544/218; 544/219; 544/232; 544/238; 544/239; 544/240; 544/241; 544/237; 544/243; 544/244; 544/284; 544/286; 544/287; 544/288; 544/296; 544/300; 544/302; 544/310; 544/311

[58] Field of Search ............... 525/61, 149, 154, 157, 525/351, 359.2; 544/194, 218; 8/540

[56] References Cited

U.S. PATENT DOCUMENTS 3,055,895  9/1962  Joyce et al. .......................... 260/248
3,108,029 10/1963  Wohnsiedler et al. ............. 156/330
3,152,181 10/1964  Shapiro et al. ....................... 260/564
3,696,102 10/1972  Cronin ........................... 260/251 QA
4,178,448 12/1979  Adams et al. ......................... 544/194

Primary Examiner—Joseph L. Schofer

Assistant Examiner—Bernard Lipman

[57] ABSTRACT

The invention provides amidoxime derivatives of the general formula

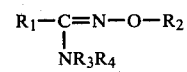

wherein $R_1$ is an alkyl group of 1 to 8 carbon atoms, phenyl, a heterocyclic ring structure of 5 to 8 atoms containing one or more nitrogen or oxygen atoms or combinations thereof or a bicyclic condensed ring system optionally containing at least one heterocyclic ring which groups may each be optionally substituted. $R_2$ is a mono or bicyclic heterocyclic radical containing at least two nitrogen atoms which radical is also optionally substituted. $R_3$ and $R_4$ are independently H, or an alkyl of 1 to 4 carbon atoms or one, but not both, is

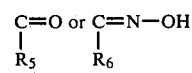

and the other, H, wherein $R_5$ or $R_6$ are alkyls of 2 to 5 carbon atoms optionally substituted by $R_1$, or a phenyl optionally substituted by $R_1$ or $R_5$ or $R_6$ is combined with $R_1$ to jointly form cyclic imidoximes or imidedioximes. The invention also provides processes for the preparation of these compounds and many uses therefor including application in affinity chromatography, enzyme reactors and for preparing dense and porous fibers, fabrics, and particles.

52 Claims, No Drawings

AMIDOXIME DERIVATIVES, PROCESSES FOR THE PREPARATION

The present invention relates to novel amidoxime derivatives, processes for the preparation thereof and uses therefor.

More particularly the present invention relates to novel compounds of the general formula I $$R_1-C(NR_3R_4)=N-O-R_2$$

wherein $R_1$ is H, an alkyl group of 1 to 8 carbon atoms, phenyl, a heterocyclic ring structure of 5 to 8 atoms containing one or more nitrogen or oxygen atoms or combinations thereof or a bicyclic condensed ring system optionally containing at least one heterocyclic ring as defined, which groups may each be optionally substituted by one or more groups as hereinafter defined and enumerated, or $R_1$ is a monomer unit repeated many times forming a polymer or macromolecule, with itself and/or other monomers and the remainder of formula I attached to $R_1$ are repeating pendants of the said polymer.

$R_2$ is a mono or bicyclic heterocyclic radical containing at least two nitrogen atoms of cyclic carbonic acid imide derivative structures, which is also optionally substituted by one or more groups as hereinafter defined.

$R_3$ and $R_4$ are independently H, or an alkyl of 1 to 4 carbon atoms or one, but not both, is $$-C(R_5)=O \text{ or } -C(R_6)=N-OH$$

and the other, H, wherein $R_5$ or $R_6$ are alkyls of 2 to 5 carbon atoms optionally substituted by $R_1$, or a phenyl optionally substituted by $R_1$ or $R_5$ or $R_6$ is combined with $R_1$ to jointly form cyclic imidoximes or imidedioximes.

The novel process according to present invention comprises reacting an amidoxime of the structure:

$$R_1-C(NR_3R_4)=N-OH$$

with a compound of cyclic carbonic acid imide halides referred to as the formula $R_2$-Hal wherein $R_1$, $R_2$ and $R_4$ are as defined herein to form a compound of the formula $$R_1-C(NR_3R_4)=N-O-R_2$$

As is known, the amidoxime function contains an amine or amine derivative and an isonitroso group on a carbon radical, e.g.

$$R_1-C(NH_2)=N-OH$$

It has now been found that the isonitroso group of amidoximes in general will react via a nucleophilic displacement of a halide radical of a compound designated for this purpose as $R_2$-Hal, wherein $R_2$ is as defined herein and Hal designates the reactive leaving halogen group to give compounds of the general formula I, and thus a whole new line of heretofore unknown amidoxime derivatives can be produced according to the present invention.

As far as can be determined, the prior art does not teach or suggest the presently claimed reaction of amidoximes and compounds of the formula $R_2$-Hal and thus the presently claimed process also constitutes a major advance in the art.

The reaction kinetics and degradation mechanism of amidoximes, however, with other electrophilic reagents (e.g. acyl, phosphonyl and sulfuryl halides) is described, and has been shown to be significantly different than the reaction of electrophilics with oximes, aldoximes and hydroxamic acid (J. D. Aubart and R. F. Hudson, Chemical Communications, 1969, p. 1342, and R. F. Hudson and R. C. Woodcock, Leibigs Ann. Chem. 1978, p. 176-186). This difference is attributed to the amine function promoting intramolecular catalysis. Thus, the already patented product of triazine derivatives with aldoximes and their use as herbicides (Brit. Pat. No. 1318514, May 31, 1973) is basically different than that of the present invention.

In light of the large number of known amidoxime functions, as enumerated, e.g. in the article *The Chemistry of Amidoximes and Related Compounds*, F. Eloy and R. Lenaers, Chem. Review 62, p. 155-183, 1962, and the numerous $R_2$-Hal type compounds, some of which are cited in the book *Fiber Reactive Dyes*, by W. F. Beech, Logos Press Limited, 1970, to which the novel process of the present invention can readily be applied, it will be realized that the present invention provides a large class of novel compounds, the numbers of which class will find many diverse uses including those mentioned hereinafter.

Thus, the present invention provides compounds of the formula I $$R_1-C(NR_3R_4)=N-O-R_2$$

wherein $R_1$ is H, an alkyl group of 1 to 8 carbon atoms, phenyl, a heterocyclic ring structure of 5 to 8 atoms containing one or more nitrogen or oxygen atoms or combinations thereof or a bicyclic condensed ring system optionally containing at least one heterocyclic ring as defined, which groups are optionally substituted by one or more halogen, amine, alkylamine, dialkylamine, amidoxime, substituted alkylamine, hydroxy, alkoxy, nitroxide, branched and straight chain alkyl, nitro, cyano, carboxamide, carbonyl, carboxyl, sulphonamide, sulphonimide, phosphonyl, sulphonyl, oxime, amidoxime optionally substituted with a mono or bicyclic heterocyclic radical containing at least two nitrogen atoms which radical itself is optionally substituted by halogen groups; polymeric radical of the structure

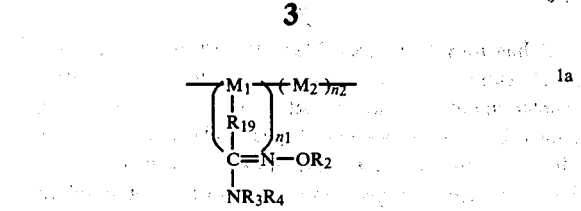

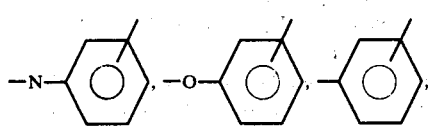

wherein $R_{19}$ is attached to the carbon atom of formula I and is a valence bond, an alkyl group of 1 to 4 carbon atoms, or a group of the formula $-O-(CH_2)_{\overline{p}}$ or $-N-H-(CH_2)_{\overline{p}}$ where p is 1–6, or

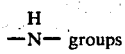

$n_2$ is 0 or a whole number defined by the polymers molecular weight and its relationship to $n_1$ defined by the ratio of $n_2$ to $n_1$, which may take values from 0 to 20. The $n_1$s and $n_2$s are randomly distributed or distributed in blocks in the polymer backbone and $M_1$ and $M_2$ are olefins wherein $M_2$ may be the same or different monomers, such that $M_1$ and $M_2$ form co, ter, tetra or penta polymers or $M_1$ and $M_2$ are cellulosics or polysaccharides or $M_1$ and $M_2$ are polysulfones, polyphenyleneoxides, polyamider or epoxy type polymers, respectively, wherein the polymer molecular weight may vary from 200 to 5,000,000 or to such a molecular weight considered infinite as may be defined by a crosslinked solid or gel.

$R_2$ is a mono or bicyclic heterocyclic radical of cyclic carbonic acid imide derivatives containing at least two nitrogen atoms, and optionally substituted alone or in combination with radicals of halogens, $-NH_2$, mono and dialkyl amino of 1 to 6 carbons per alkyl chain, anilino, naphthylamino, $-OH$, alkoxyl of 1 to 6 carbons, aryloxy; coloured and non-coloured tertiary amines, hydroxy, alky ammoniums of 1 to 6 carbons per alkyl chain, sulfonium, phosphoniums and carboxylic, sulfonic and phosphonic acid derivatives of mono and dialkyl amino, anilino, naphthyl amino, alkoxyl and aryloxy radicals; $-SH$, alkylthio of 1 to 6 carbon atoms, alkyl (1 to 6 carbons), arylthio, hydrazine, $-CN$, phosphonic esters, $-SO_2NH_2$, arylsulfonamides, $-SO_3H$, phenylalkyl; synthetic or biological oligomers or polymers, which are substituted in $R_2$ through amino (alkyl or aryl) groups, hydroxyl (alkyl or aryl), sulfhydryl groups or heterocyclic $$-\overset{H}{N}- \text{ groups}$$

on the synthetic or biological oligomers or polymers, which polymeric groups optionally include additional $R_2$ groups which $R_2$ groups are themselves attached to an amidoxime on the same or different amidoxime polymers through $R_{19}$; and diamidoxime groups, which amidoxime groups themselves optionally are substituted by the hereinbefore defined substituents of $R_1$ and said diamidoxime groups are themselves optionally linked to a further $R_2$ group as hereinbefore defined forming an alternating polymeric structure of diamidoxime and $R_2$ groups.

$R_3$ and $R_4$ are preferably, independently H for the polymeric structures defined by 1a, or for low M.W. compounds independently H, or an alkyl of 1 to 4 carbon atoms or one, but not both, is

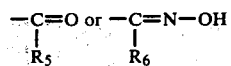

and the other, H, wherein $R_5$ or $R_6$ are alkyls or 2 to 6 carbon atoms optionally substituted by $R_1$, or a phenyl optionally substituted by $R_1$ or $R_6$ and $R_1$ together form structures of the formulas

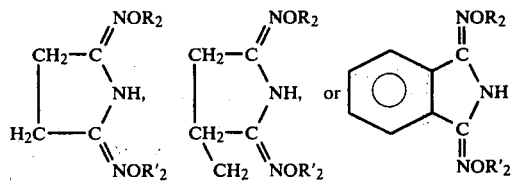

wherein $R_2$ is as defined and wherein $R'_2$ is either $R_2$ or H, or wherein $R_3$ is H and $R_4$ is

and $R_5$ and $R_1$ together form structures of the formula:

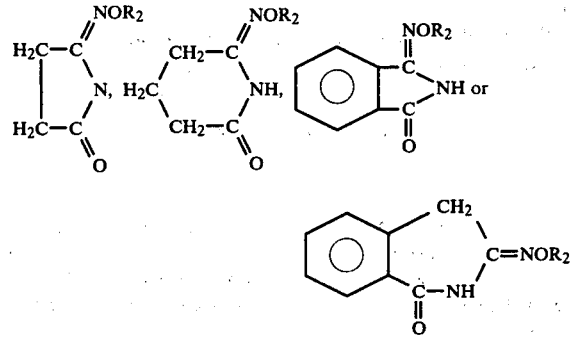

wherein $R_2$ is as defined.

Referring first to the $R_2$-Hal compounds, said compounds can be selected from a wide range of suitable compounds including, but not limited to:

(a) Symmetrical and unsymmetrical triazines containing at least one halogen atom or two or three identical or different halogen atoms bonded to carbon atoms, for example, cyanuric chloride, cyanuric fluoride, cyanuric bromide and also primary and secondary condensation products, of cyanuric fluoride or cyanuric chloride or cyanuric bromide and, optionally further substituted, e.g. by carboxyl, cyano, carboxamide, sulphonamide, secondary, tertiary, quaternary alkyl or aromatic amines, alkoxy, hydroxy, alkylthiol, phenol or thiophenol, amidine, pyridine groups, (b) Diazines such as pyrimidines, pyridazines and pyrazines containing at least one reactive halogen atom or two or three reactive identical or different halogen atoms, such as 2,4,6-trichloro-, 2-4-6-trifluoro- or 2-4-6-tribromopyrimidine, which can be further substituted by groups, for example, by an amine, hydroxyl, quaternary ammoniums, alkyl or aromatic amines, alkyl thiols, aldehyde, phenyl, carboxyl, cyano, nitro, chloromethyl, chlorovinyl, carbalkoxy, carboxymethyl, alkylsulfonyl, carboxamide or sulfonamide group. Suitable halogenopyrimidines, for example, are 2,4,6-trichloro- and 2,4,5,6-tetrachloropyrimidine and 2,4,5-trifluoro-5-chloro-pyrimidine;

(c) Halogenpyrimidinecarboxylic acid halides, for example, dichloropyrimidine-5 or 6-carboxylic acid chloride;

(d) Quinoxaline, quinazoline or phthalazine substituted in the heterocyclic or aromatic ring portions, by carboxylic acids, sulfonic acids, halogens (Cl or Br), amino, alkoxy, carboxyl cyano, sulfonamide, amides, etc., e.g. 2-3-dihalogeno quinoxaline-, quinazoline- or -phthalazine- carboxylic acid halides or -sulfonic acid halides, such as 2,3-dichloroquinoxaline-6-carboxylic acid chloride or -6-sulfonic acid chloride, 2-6-dichloro-quinazoline-6- or -7-carboxy 7-carboxylic acid chloride and 1,4-dichloro-phthalazine-6-carboxylic acid chloride or acid bromide;

(e) 2-halogeno-benzthiazole- or -benzoxazole-carboxylic acid halides or -sulfonic acid halides, such as 2-chlorobenzthiazole- or -benzoxazole-5- or 6-carboxylic acid chloride or -5- or -6-sulfonic acid chloride; and (f) Halogeno-6-pyridazonyl-1-alkanoyl halides or 1-benzoyl halides, for example, 4,5-dichloro-6-pyridazonyl-1-propionyl chloride or -1-benzoyl chloride.

It should be emphasized that the substituents of $R_2$ are not always defined by $R_2$-Hal. In effect, relative substituents of $R_2$ (e.g. —CL, or —$NH_2$) may be further reacted to a new product, wherein both the initial reactant and final product are defined by formula I. Thus, $R_2$ is derived from cyclic carbonic acid imide halide structures, some preferred compounds are those in which $R_2$ is:

(a) an optionally substituted radical of a six-membered ring containing at least two nitrogen atoms; or (b) an optionally substituted bicyclic condensed ring system containing at least one six-membered ring of at least two nitrogen atoms.

Such compounds include a 1,3,5-, 1,2,3- or 1,2,4-triazinyl, pyridazinyl, pyrimidyl, pryrazinyl, pyridazonyl, quinoxalinyl, phthalazinyl or quinazolinyl radical, optionally substituted as described with, for example, halogens or —COOH, —CN, —$CONH_2$, —$SO_2NH_2$, —$NR_7R_8R_9$, or —$OR_{10}$, or —$SR_{11}$, wherein $R_7$ is H, $R_8$, $R_9$, $R_{10}$ and $R_{11}$ are independently H or alkyl chains with 1 to 6 carbons or anilino or anilino derivatives with carboxylic sulfonic acid groups or secondary, tertiary or quaternary ammonium groups, or pryimidyl radical optionally substituted by, for example, at least one group selected from halogen, amines, alkylamines, dialkylamines, anilino derivatives as described, alkoxy and alkylthiol, alkyl, carboxyl, cyano, carboxamide, and sulfonamide groups; and especially include a triazinyl or pyrimidyl, substituted by at least one reactive halogen and by a —$NR_7R_8R_9$ or anilino or anilino derivative group or a triazinyl or pyrimidyl substituted by at least one halogen and by a —$OR_{10}$ or —$SR_{11}$ group; and a 1,3,5-triazinyl or a pyrimidyl substituted by an additional amidoxime radical of the formula

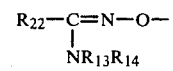

wherein $R_{22}$ independently has one of the values of $R_1$ and $R_{13}$ and $R_{14}$ are independently H or an alkyl of 1 to 4 carbon atoms.

Amidoxime compounds may be aryl or aliphatic amidoximes as, for example, described in, but not limited to, *The Chemistry of Amidoximes and Related* Compounds (F. Eloy and R. Lenaers Chem. Review 62, 1962, p. 155-183). The compounds may contain one, two, three or any number of amidoximes including polyamidoximes, or copolymers of polyamidoximes.

In the latter category are included alkylenediaminetetraacetamidoximes (U.S. Pat. No. 2,902,514) or polyamidoximes or copolymers containing amidoxime radicals as pendents or within the polymer backbone independent of the mode of synthesis of the said amidoxime polymer. Specifically such polymers may be derived from any polymer containing nitrile groups as pendants on a polymeric backbone (for example, polyacrylonitrile and its copolymers, cyanoethylated polyvinyl alcohol and polyvinylamine, poly(amino alkyl(meth) acrylates), polysaccharides, cyano methylated or alkylated polysulfone or cyanomethylated or alkylated polyphenylene oxides, etc) (GB 786,960), sterically unhindered cyano derivatives of polystyrene, polyamides and epoxies, or polymeric substances containing amidoxime function as an integral part of the backbone (Hong-Suck-Jri; Shen Yound-Jin, Taehan Hwahak Hoechs, 1974, 18 (6) 453-J (Eng).

As can be learned from said Chem. Review article ibid., many amidoxime functions are already known and have been prepared and accordingly $R_1$ could have any of the values mentioned for R in Tables 2, 3 and 4 of said article without interferring with the process of the present invention, and thus compounds according to formula I wherein $R_1$ can be e.g. any of said values are included in the scope of the present invention.

With regard to the compounds of Table 4 of said article, it is to be noted that the present invention also includes, as amidoxime derivatives, which can be reacted with $R_2$-Hal compounds to form the novel compounds of formula I, imidoximes and imidedioximes such as those having the formulas:

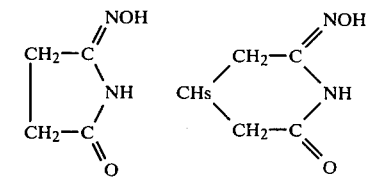

(a)        (b)

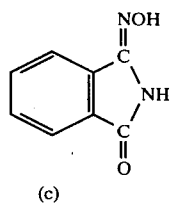 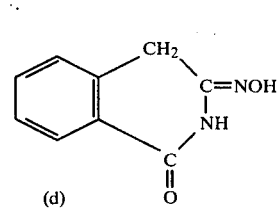

(c)        (d)

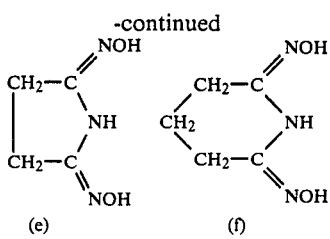

(e)   (f)

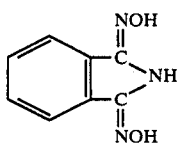

(g)

When said above mentioned amidoxime derivatives are reacted with $R_2$-Hal compounds there are preferrably produced compounds according to formula I, wherein:

(a) $R_3$ is H and $R_4$ is

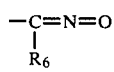

and $R_6$ together with $R_1$ form structures of the formula

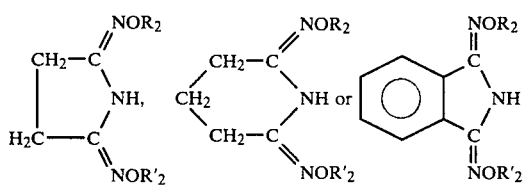

in which $R'_2$ is H or $R_2$; or (b) $R_3$ is H, $R_4$ is

and $R_5$ together with $R_1$ form structures of the formula

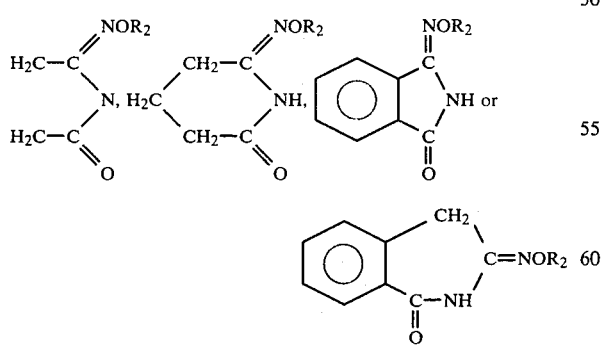

Preferrably in said compounds $R_2$ is a substituted triazinyl, pyrimidyl or quinoxaline radical as defined.

The invention also provides compounds of formula I having the structure VIII

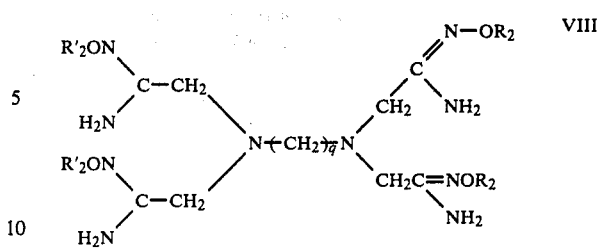

wherein each $R'_2$ is independently either $R_2$ or H, $R_2$ is a triazinyl or pyrimidal radical and q is 2, 3 or 6.

Under most conditions of amidoxime reaction with $R_2$-Hal compounds the isonitroso groups were found to react more readily than the amine group. This difference in reactivity enables the selective substitution of the isonitroso and amine functions. Thus, after O-substitution with an $R_2$-Hal compound the free amine may be reacted with other $R_2$-Hal compounds, isocyanates, thioisocyanates, benzoyl chloride formaldehyde, carbon disulfide, hydrazine, etc. Alternatively, the amidoxime compound prior to reaction with $R_2$-Hal compounds may be N-substituted with alkyl or aryl radicals, through C, O, N, P, S atoms.

The substituted groups may affect the reactivity of the amine function by any of the well known mechanisms (e.g. electron attraction or repulsion or by steric or electrostatic effects). Thus, if the amine function is substituted to form an imidoxime the reactivity of the nitrogen radical is enhanced under basic conditions and may compete with the isonitroso group during the reaction with $R_2$-Hal. Included within the scope of this invention are such N-substituted amidoximes (including the class of imidoximes) and their reaction products with $R_2$-Hal.

In addition, compounds containing both an oxime and amidoxime, e.g.

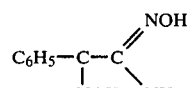

α-phenyl aminoglyoxime are included within the scope of the invention.

This invention is not limited by the method of preparing the amidoxime compounds. Synthesis procedures, however, may include:

(A) The reaction of hydroxylamine with compounds containing nitriles, amides, thioamides, amidine hydrochlorides and iminoethers;

(B) The reduction of nitrolic acids and oxyamidoximes;

(C) Reaction of ammonia with hydroximic acid chlorides, oximinoethers and glyoxime peroxides; and (D) Reaction of formamidoxime with aromatic aldehydes.

If $R_1$ and $R_2$ are mutually substituted with amidoxime functions, then polymeric structures of the formula:

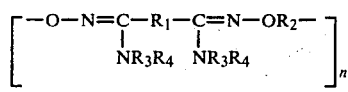

are formed.

If $R_1$ is substituted by a polymer, then structures of the following formula may form:

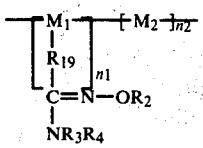

wherein $M_1$, $M_2$, $R_{19}$, $R_2$, $R_3R_4$ have the previously described meaning. If, in addition, $R_2$ is optionally substituted on an amidoxime function of another polymer, the polymeric material is also crosslinked, i.e., for example:

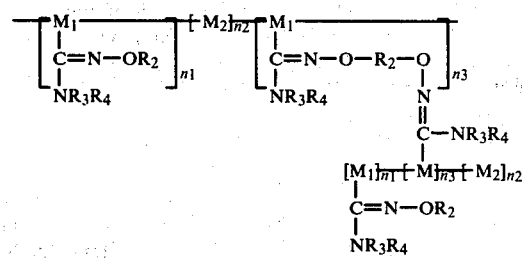

In one preferred embodiment, the polymeric pendents, $R_3$ and $R_4$ will be H, and $R_2$ a triazinyl or pyrimidyl group containing reactive halogens and $M_1$ and $M_2$ will both be olefinic.

Thus, the present invention also provides compounds of formula I, wherein $R_1$ is substituted with another radical of the formula V

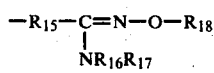

wherein $R_{15}$ independently has one of the values of $R_1$ and preferably is an alkyl of 1 to 8 carbon atoms or a phenyl optionally substituted with halogen, $R_{16}$ and $R_{17}$ are independently H or an alkyl of 1 to 4 carbon atoms and $R_{18}$ independently has one of the values of $R_2$ as well as providing polymeric compounds wherein $R_1$ is substituted with another radical of the formula V as defined and wherein $R_2$ and optionally $R_{18}$ is substituted by at least two diamidoxime groups, which groups are themselves linked to further $R_2$ groups as defined forming an alternating polymeric structure of diamidoxime and $R_2$ groups such as high molecular weight polymeric compounds formed from alternating diamidoxime and triazinyl or pyrimidyl radicals of the formula VI

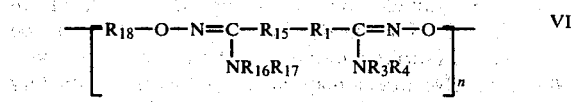

wherein $R_1$, $R_3$, $R_4$, $R_{15}$, $R_{16}$, $R_{17}$ and $R_{18}$ are as defined and n is a whole number of at least 2.

Also provided according to the present invention and especially preferred for their applicability in insolubilizing biological materials, enzyme reactors, supports for cell growth, affinity chromatography HPLC and as reactors for the synthesis of polypeptides and/or nucleotides, are high molecular weight polymeric compounds of formula IX

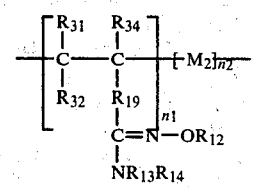

in which $R_{12}$ is a mono or bicyclic heterocyclic radical containing at least two nitrogen atoms taken from the class of cyclic carbonic acid imides which radical itself is optionally substituted in a fraction of all of $n_1$ units alone or in combination by halogen, amine, di-, tri-, alkyl amino (of 1 to 8 carbon atoms) or quaternary ammoniums, anilino- (and the alkyl amino and anilino radicals with secondary, tertiary amines, quaternary ammoniums, carboxylic, sulfonic or phosphonic acid groups), hydroxyl, alkoxy, sulfhydryl, imidazole or phenol groups or a chromophor radical, an amidoxime or a polymeric amidoxime group, or polyamines, polyalcohols, or biological materials (such as polysaccharides, proteins, peptides, lectins, antibodies, antigens, enzymes, etc), wherein said materials are bound to more than one $R_{12}$ radical on the same or different macromolecule defined by formula IX, $R_{13}$ and $R_{14}$ are preferrably hydrogen or less preferrably alkyl groups of 1 to 8 carbon atoms; $R_{19}$ is a valence bond, a phenyl, an alkyl group of 1 to 4 carbon atoms, or a group of the formula $-NH-(CH_2)_p-O-(CH_2)_p-$ where p is 1–4, $n_2$ is 0 or a whole number and $n_1$ is a whole number, wherein the ratio of $n_2$ to $n_1$ varies from 0–20, the $n_1$s and $n_2$s are randomly or in "blocks" distributed in the polymeric backbone and M may be chosen individually or in combinations from olefinic monomers, wherein the polymer molecular weight may vary from 200 to 5,000,000; $R_{34}$ is a H, or an alkyl radical of one to six carbons, preferrably H or methyl, a phenyl or a halogen; $R_{31}$ and $R_{32}$ are in most cases hydrogen, but may be independently halogens, preferrably F, or Cl, or an alkyl of 1 to 6 carbons.

In one preferred embodiment of the invention are polymeric material or compounds of the formula IX where $R_{34}$ is H or an alkyl radical of 1 to 6 carbons, a phenyl or a halogen and $R_{31}$ and $R_{32}$ are independently radicals of H, halogens or an alkyl of 1 to 6 atoms and $M_2$ is one or more olefinic different monomers, which may be chosen individually or in combinations from polymerizable olefinic monomers, and the final molecular weight $n_1+n_2$ may vary from 200–5,000,000 or to such a molecular weight considered infinite as defined by a crosslinked substance, and the ratio $n_2/n_1$ varies from 0 to 20, wherein a fraction of the total number of $R_{12}$'s is substituted in part or solely with synthetic or biological oligomers or polymers through the primary or secondary alkylamines, arylamines, hydroxy alkyl, hydroxyl aryl or sulfhydryl groups or heterocylic nitrogens of proteins, peptides, lectins, enzymes, hormones, polysaccharides, cellulosics, antibodies, antigens, polynucleotides, whole cells or cellular fragments, polyethylenimine, polyvinyl alcohol, polyvinylmidazole and poly(amino alkyl (meth) acrylate) with alkyls of 1 to 6 carbon atoms.

In such compounds $M_2$ is preferrably chosen from acrylonitrile, vinyl acetate, acrylic acid, methacrylic acid, styrene allyl sulfonate, vinyl alcohol, allyl halide, or combinations thereof and especially preferred are such compounds in which $M_2$ is a copolymer of acrylonitrile or acrylonitrile and another copolymer as defined, preferably $R_{19}$ is a valence bond, $R_{13}$ and $R_{14}$, $R_{31}$, $R_{32}$ and $R_{34}$ are H, and $R_{12}$ is a substituted triazinyl or pyrimidyl radical as defined.

In said preferred class of high molecular weight polymeric compounds $R_{12}$ is preferably a halogen substituted triazinyl or pyrimidyl radical optionally substituted with a biological polymer such as an enzyme or a synthetic polyamine such as polyethylimine (PEI) or a polyalcohol such as polyvinyl alcohol (PVA) of a molecular weight between 200 and 5,000,000 and said enzyme, PEI or PVA molecule is optionally bound to more than one $R_2$ radical.

Similarly, wherein $R_1$ is a polyolefinic radical of the structure IX ad defined, compounds wherein $R_{12}$ is a radical derived from active dyes, such as reactive dyes based on triazinyl, pyrimidyl, quinoxaline-6-carbonyl, pyridazonyl, propionyl, 1,4-dichloro-phthalazine-6-carbonyl or benzothiazole, are preferred.

Examples of $R_1$ being substituted via a polymeric backbone are:

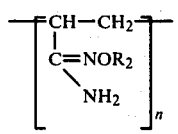

or as a co, tri, ter, etc. polymer, for example:

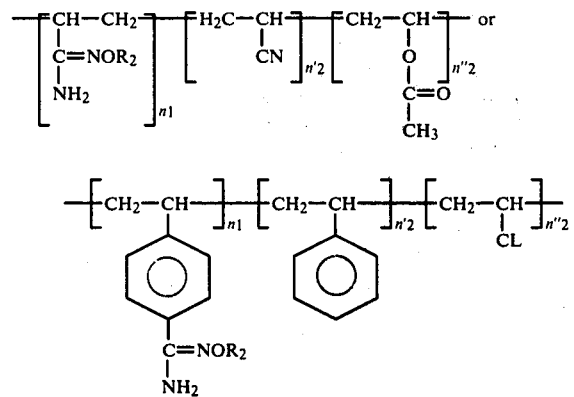

One class of preferred polymers, from which the material of the invention may be derived, as a rule consists of polyacrylonitrile co or tri polymers, in which case the proportion of acrylonitrile units in the copolymer is at least 5, preferably at least 20 and in particular at least 50%. Further suitable polymers (in addition to polyacrylonitrile) are those of alkyl ($C_1$-$C_6$)-acrylonitriles, for example, methacrylonitrile or hexylacrylonitrile, acylacrylonitriles, for example, phenylacrylonitrile, halogenoacrylonitriles, in which halogen is fluorine, chlorine or bromine, for example, α-fluoroacrylonitrile or α-chloroacrylonitrile, and thioacrylonitriles. Another class of suitable polymers are polystyrene co or tri polymers containing cyano substitutents on the aromatic ring.

Suitable comonomers which can be copolymerized with acrylonitrile are monomers which contain, for example, hydrophobic, hydrophilic, polar or ionic groups, especially, for example, vinyl esters having 2 to 18 carbon atoms in the acid moiety, especially vinyl acetate, vinyl ethers having 3 to 12 carbon atoms, vinylpyridine, vinyl chloride, styrene, butadiene, acrylic acid or (meth)arcylates, for examples, those having 1 to 4 carbon atoms in the ester moiety. Further suitable monomers are maleic anhydride, diallylamine 2-aminoethyl methacrylate and allyl compounds, for example, allyl alcohol, allyl- or methallyl-sulfonic acid and their salts (alkali metal salts), allyl halides or methallyl halides, allylamines or allyl p-toluenesulfonates. Further suitable compounds are terpolymers, for example, of acrylonitrile, styrene and butadiene (ABS polymers), acrylonitrile/vinyl acetate/methylmethacrylate or acrylonitrile/methyl methacrylate/sodiumallylsulfonate or tetrapolymers based on acrylonitrile.

The novel compounds of the present invention have many uses. For example, the low molecular weight compounds may be used to modify fibers, particles,-weaves, nets and clothes containing amidoxime, oxime, cyano, hydroxy, amine, carboxyl, thiol and sulphonamide groups, such as acrylics, cellulosics, wool and nylons, if $R_2$ is substituted with reactive halogens. If the compounds are polymeric pendents, where —$R_2$ is a reactive dye pendent, then this invention may be used for dyeing nitrile containing fibers or clothes. If the $R_2$ group is bound to two different chains via amidoxime groups, then by this invention acrylonitrile fibers are crosslinked and strengthened. If $R_2$ contains further reactive groups (e.g. halogens) for binding biological materials such as enzymes, hormones, lectins, antibodies, antigens, amino acids, nucleotides, whole cells and cell fragments and other biological molecules or catalytic agents, or functional groups (such as amino) to which cells may adhere and grow, then this invention may be used to produce films, particles or fibers (small configurations dense or porous), (the fibers may be bundled or singular, or as a fabric or cloth) useful in flow cytometry, phagocytosis, immunological markers, affinity labelling trucer studies, solid phase radioimmunoassay clinical test kits, affinity chromatograph, enzyme reactors HPLC and substrates for the production of polypeptides and/or polynucleotides and as structures where upon cells may adhere for cell culture devices.

In addition, if —$R_2$ contains reactive groups for binding hydrophilic polymers, then antistatic and hydrophilic properties may be imparted to hydrophobic films, fibers and particles. Such coated materials may also find application in affinity chromatography, enzyme reactors and substrates for polypeptides and/or polynucleotides by binding reagents or enzymic or biospecific adsorbents through the groups on the hydrophilic polymers. In the case of affinity chromatography, some hydrophilic coatings may minimize nonspecific adsorption.

Thus, if the amidoxime of formula II (pg. 21) is already a polyamidoxime of the type described, e.g. in Brit. Pat. No. 786,960 $R_2$-Hal compounds may also be reacted as described above and, therefore, polyacrylonitrile (PAN) fibers may be partially or completely modified to form fibers containing amidoxime groups on a polymeric backbone. In this way, PAN fibers may be dyed with reactive dyes because $R_2$-Hal derivatives form a large class of such reactive dyes (S. F. Beech "Fiber Reactive Dyes", 1970, Logos Press Ltd). Alternatively, the product of a polyamidoxime and an $R_2$-Hal compound may be subsequently reacted with a water attracting monomer or polymeric substances to impart antistatic or hydrophilic properties to the PAN fiber. Futhermore, fire-retarding, softening or antistatic agents to which a $R_2$-Hal function is attached may react with the amidoxime modified PAN textile to result in permanent fire-retarding, softening or antistatic effects. For example, PAN fibers may be reacted with hydroxylamine under controlled conditions that convert the surface nitrile groups to amidoxime functions. The fiber may then be dyed with, for example, triazinyl, pyrimidyl or quinoxaline type reactive dye. Alternatively, the amidoxime group may be reacted with 2,4,6-trichloro 1,3,5-triazine or tetrachloro pyrimidine under conditions where only one or two reactive chloro has reacted. The remaining chloro groups may subsequently be reacted with a water attracting monomer or polymeric substances (e.g. polyvinyl-alcohol) to impart antistatic or hydrophilic properties to the PAN fiber. It should be noted that while PAN materials are given as an example, any polymeric material may be modified by the process of this invention if it contains as pendants or incorporates withing the backbone an amidoxime or $R_2$-Hal group.

In light of the above, the present invention also provides methods for preparing novel fibers, both dense and porous, fabrics of such fibers and particles, both dense and porous. The porosity may vary from 1% to 99% of the total volume. The preferred range depending on the application. And the particles and/or fibers may be transparent, translucent or opague in the dry or wet state.

Thus, substrates such as fibers and particles composed of polymers containing nitrile pendants (ex. polyacrylonitrile and its copolymers) can be modified by the sequence taught in this invention, to give the composition of matter also claimed. In effect, hydroxylamine converts the nitriles to amidoxime functions and the said amidoxime functions are then reacted with $R_2$-Hal compounds. The resultant material contains structures described with regard to formula I. For the example of polyacrylonitrile after the hydroxylamine has reacted with cyanuric chloride or, for example, a mono alkyl amino or anilino dichloro triazinyl, the structure formed is:

dichloro triazinyl or 2-anilino, 4,6-dichloro triazinyl, respectively.

The resultant materials may then be substituted further on the unreacted halogen or reactive groups (e.g. —$NH_2$ or OH) of the triazinyl substituent. For example, the above product may then be reacted with biological materials or alternatively water soluble reactive polymers such as: polyethylenimine, polyvinylamine, polyvinyl alcohol or a water soluble polysaccharide, thus, in effect, coating and binding to the fiber or particle or films of these materials. Further reactions may then be carried on the uncoated or coated fibers or particles to bind lectins, hormones, enzymes, antibiotics, peptides, ammoacids, nucleotides, etc. from whole cells, cell fragments, from microbial, fungi, yeast algea, plant or animal sources.

In another variation, cells, cellular fragments may be reacted directly to the compounds of formula I through the unreacted halogen without the intermediate hydrophilic polymer layer. In this and the above cases, the substrates, such as fibers or particles may be used in affinity chromatography, enzyme reactors and supports for the synthesis of polypeptides and polynucleotides, as well as supports for cells in culture devices. In the latter case, cells may be physically adsorbed and not chemically bound. To achieve such an adsorption the unreacted halogen may be reacted with compounds containing functional groups that are known to adsorb cellular structures, as for example, quaternary ammonium groups.

The fibers or particles, which may be modified by the process of this invention may have diameters varying from $0.1\mu$ to 5 mm, but the preferred range varies with the application. For example, for the tagging of cells with fluorescent or chromophoric material a range of 0.1 to $1.0\mu$ may be preferrable, while for an enzyme reactor the range of 200–$500\mu$ is preferrable and so on. The particles or/and fibers, or substrates in general, may be dense or porous, wherein the pore size may be from 10A° to 10000A° including the class of particles called macroreticulate and porosity or pore volume may vary from 1% to 99%. The fibers may have a similar range of porosity and as an example of the po-

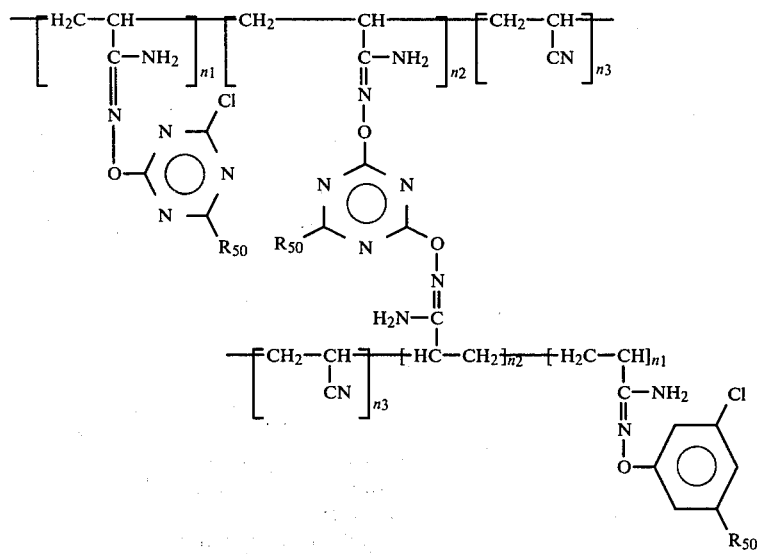

where $R_{50}$ is CL if $R_2$-Hal if cyanuric chloride or $R_{50}$ is alkyl amino or anilino- if $R_2$-Hal is 2-alkyl amino, 4,6- rous fiber, is the Bayer acrylonitrile fiber Dunova ®. The fibers may be of any length 1μ to 10 kilometers. Thus, any nitrile containing polymer, which may be formed into fibers or particles is suitable for further modification by the process of this invention.

In certain applications porous particles or fibers may be more desirable than dense materials. For example, in enzyme reactions a higher quantity of enzymes per gram of material is achieved with porous fibers and particles and this is reflected in a more favorable economics of the processes. In the application to affinity, chromatography dense structures with a layer of a hydrophilic polymer may be bound through the $R_2$-Hal group to the support. The molecules with the required biological affinity may then be bound. On the other hand, support materials for polypeptide of polynucleotide synthesis require high reactive group capacity, and thus, porous materials are favored.

The fiber may be in the form of individual fibers or a woven or non-woven fabric. The fabric may be a monofilament or multifilament and the filaments may be arranged in the fabric as a plain weave, twill weave, calendered, half gauze imitation, reverse plain dutch weave, leno weave (full or half gauze) without limiting it to these arrangements. The apertures in the fabric may vary between $0.1\mu$ to $5000\mu$, but in most applications the desired range will be between $4\mu$ to $200\mu$, though lower ranges may also be very desirable in some cases. The aperture size may affect the kinetics of a process based on this invention. For example, if a solution of substrate is passed through the net or fabric in an enzyme reactor under pressure, apertures less than $10\mu$ will minimize the unstirred layer affect, which often is the rate limiting step with fast enzymatic process carried out on particles or solid substrates. Thus, apertures less than $4\mu$ may be desirable, especially for relatively dilute solutions. If, on the other hand, highly concentrated viscose solutions are used, larger apertures are required to minimize clogging.

The fabric may be arranged for a process as layers placed on top of each other to form a depth filter on a support, and pressure applied from the top to the bottom, or placed in a plate and frame device or in a filter press, or would in a spiral wound configuration. The solution to be treated may then pass transversely through the fabric or fabric layers or may pass over the surface and between the layers of the fabric. The fibers may also be placed in a bundle of any size and placed in a holder where the ends are potted. The solution to be treated may then pass over the surface and between the individual fibers. The term fiber is meant to include configurations without or with a lumen, wherein the latter is known as a hollow fiber, wherein solutions may be passed through the fiber. In the case of particles, the said particles may be placed in a column or in a reaction vessel and used under flow through conditions in a continuous process or batch operations.

In one embodiment of the invention, the starting materials (particles or fibers) are treated for 3 min to 48 hours at temperatures of 0° to 95° C. with an aqueous solution of hydroxylamine (0.2 to 80%, but preferably 1 to 20%), which has a pH value of 2 to 11, but preferably to 6 to 7 (adjusted with sodium carbonate). The efficiency of conversion of nitrile to amidoxime groups can be from 0.5 to about 80% and preferable in the range of 1.0 to 22%, for example, for polymers containing 80% or more of acrylonitrile units. The particles or fibers may then be placed in an aqueous solution (suspension) or an organic solution (ex. acetone, dioxane, N,N' dimethyl formamide, chloroform, methylene chloride, N-methypyrrolidone) of an $R_2$-Hal compound. For example, cyanuric chloride is a suspension of 0.5 to 5 parts in $H_2O$, or 2-diethylamino-4,6-dichlorotriazine in acetone water 80/20. The reaction mixture is kept below 10° C. (i.e. 0° C.) in order to prevent hydrolysis of the cyanuric chloride; the pH value is approximately between 4 to 10, but preferably 6–8 and the reaction time can be from 10 seconds to 5 hours. If tetrochloro pyrimidine is used, then higher temperatures, longer reaction times and higher pH's may be necessary to achieve the same degree of substitution. If other $R_2$-Hal reagents are used, different reaction times may be necessary. One preferred $R_2$-Hal is an amino or anilino dichlorotriazinyl compounds.

When this invention is practiced on solid polymeric supports containing nitrile function (as previously specified), the amount of reactive halogens (in most cases Cl) introduced prior to binding biological materials or synthetic polymers, may vary between 0.05 to 3.5 meq/gr, but preferably between 0.2 to 2.5 meq/gr (dry basis).

As stated, the general novel process of the process of the present invention comprises reacting an amidoxime of the structure II

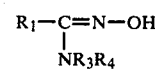

with a compound of the formula $R_2$-Hal to form a compound of the formula I

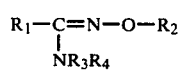

wherein $R_1$, $R_2$, $R_3$ and $R_4$ are as hereinbefore generally and specifically defined and as exemplified in the examples hereinafter.

Preferably in said process $R_2$-Hal is selected from the group consisting of a halogen substituted 1,3,5-, 1,2,3- or 1,2,4-triazinyl, pyridazinyl, pyrimidyl, pyrazinyl, pyridazonyl, quinoxalinyl, phthalazinyl or quinazolinyl radical, optionally substituted, but not limited to, with additional halogen —COOH, —CH, —CONH$_2$, —SO$_2$NH$_2$, —NR$_7$R$_8$R$_9$, anilino and anilino derivatives (containing secondary, tertiary amine or quaternary ammonium carboxylic or sulfonic acid groups), —OR$_{10}$, or —SR$_{11}$ groups, wherein $R_7$ is H and $R_8$, $R_{10}$ and $R_{11}$ are independently H or alkyl chains with 1 to 6 carbons and especially preferred for use in said process is the reacting $R_2$-Hal compound is cyanuric chloride, tetrachloropyrimidine or a mono- or di- substituted derivative thereof, wherein said substituents are selected from the group consisting of amine, hydroxy alkylamines, alkylamines, anilino and anilino derivatives, alkoxy or alkylthio groups, wherein said alkyl groups contains 1–4 carbon atoms.

As realized, the choice of the reacting amidoxime derivative of formula II and the $R_2$-Hal compound will determine the nature of the final novel compound of formula I, which is formed.

Thus, in several preferred embodiments the reacting amidoxime is acetamidoxime or benzamidoxime.

In another preferred embodiment a diamidoxime of the formula

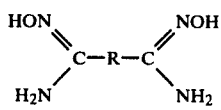

is reacted with a compound of the formula $R_2$-Hal, wherein R is a phenyl group optionally substituted by at least one Cl group or a radical of the formula $-(CH_2)_n$ and n=1 or 6.

Polymeric compounds of formula IV a defined hereinbefore can, thus be prepared by reacting a diamidoxime with a compound of the formula $R_2$-Hal, wherein $R_2$-Hal contains at least two reactive halogen groups and preferrable in such reactions $R_2$-Hal is cyanuric chloride or tetrachloropyrimide, or a mono, preferrably deactivating, derivatives of such compounds, as for example, amino alkyl derivatives.

Similarly a polymeric compound of formula IX, as defined, hereinbefore can be manufactured by reacting an olefinic polymer containing nitrile groups with a hydroxylamine and then subsequently reacting the product thereof with $R_2$-Hal.

In said process for producing polymeric compounds formula IX, preferrably $R_2$-Hal is cyanuric chloride or a mono substituted derivative such as monoamine dichloro triazine derivative or tetrachloropyrimidine or its derivatives containing at least two active halogens, and the nitrile containing polymer may be polyacrylonitrile or a copolymer of polyacrylonitrile or polymethacrylonitrile with a vinylacetate, acrylic acid, methacrylic acid, allyl bromide, acrylic acid or allyl sulfonate, wherein the comonomer may be chosen from additional compounds.

Once said products are produced, wherein the compounds of formula I are in fact polymeric compounds of formula IX as defined, the present invention can preferrably include the further possible steps of either:
 (a) reacting a water soluble polymer containing amino or hydroxyl groups with unreacted halogen substituents of the $R_{12}$ radical of compounds of formula IX, wherein the water soluble polymer is preferrably selected from polyethyleneimine, polyvinyl alcohol, polyvinylamine, or water soluble polysaccharides; or
 (b) reacting an enzyme with unreacted halogen substituents of the $R_{12}$ radical of compounds of formula IX; or
 (c) reacting a lectin, a hormone, an amino acid, a polysaccharide, a polypeptide, an antibody, an antigen, a whole cell or cellular fragments with unreacted halogen substituents of the $R_{12}$ radical of compounds of formula IX; or
 (d) reacting the unreactive halogen with primary or secondary low molecular weight amines or alkyl amino or anilino derivatives containing amines or quaternary ammoniums, or with polymers as in (a) and using such materials for cellular adsorption in cell culture devices.

The possibility of carrying out these further preferred process steps is preferrably made possible by carrying out the initial reaction of $R_2$-Hal compound with the amidoxime under conditions whereby the reaction occurs with one or two halogens of $R_2$-Hal leaving 0.1 to 3.0 meq/gr remaining of halogen substituents of $R_2$ unreacted.

In another preferred embodiment of the process of the present invention for producing polymeric compounds of formula IX the reacted $R_2$-Hal compound is a reactive dye based on symmetrical and unsymmetrical triazines and diazines such as pyrimidines, pyridazines, pyrazines, quinoxalines, quinazolines and benzothiazoles.

As stated hereinbefore, the present invention may be used to modify fibers, fabrics, particles, etc. and accordingly in another preferred embodiment of the present invention involving the polymeric compounds of formula IX and wherein as olefinic polymer containing nitrile groups is first reacted with a hydroxylamine and then the product of said reaction is reacted with an $R_2$-Hal compound, the original nitrile polymer is in the form of film $5\mu$ to 1 mm thick or a fiber $0.1\mu$ to 1 mm (preferrably 1 to $100\mu$) in diameter, fabric of such fibers or a particle $0.1\mu$ to 5 mm in diameter depending upon application, which particles or fibers or films can be porous or dense.

Thus, also in this embodiment it is preferred for some cases that the $R_2$-Hal compound be a reactive dye based on symmetrical and unsymmetrical triazines and diazines whereby the particle fiber or fabric is in fact dyed by the process of the present invention.

Similarly when a compound of formula I is prepared, as described, from an olefinic polymer containing nitrile groups and the original nitrile polymer is in the form os a fiber $1\mu$ to 1 mm in diameter, a fabric of such fibers or a particle $1\mu$ to 5 mm in diameter, then said compound can be put to several additional uses by carrying out the further steps of:
 (a) reacting a water soluble polymer containing amino or hydroxyl groups with unreacted halogen substituents of the $R_{12}$ radical of compounds of formula IX, wherein the fiber, fabric or particle is made hydrophilic; or
 (b) reacting an enzyme with unreacted halogen substituents of the $R_{12}$ radical of compounds of formula IX; or
 (c) reacting a lectin, a polysaccharide, a hormone, an amino acid, a polypeptide, an antibody, an antigen, a whole cell or cellular fragments with unreacted halogen substituents of the $R_{12}$ radical of compounds of formula IX.

While the invention will now be described in connection with certain preferred embodiments in the following examples, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples, which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

The following tables indicate structures of compounds prepared according to Examples 1-6 hereinafter:

TABLE 1

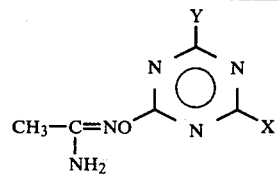

| Compound No. | X | Y |
|---|---|---|
| 1 (Ex. 1) | Cl | Cl |
| 2 (Ex. 2) | —NHCH₃ | Cl |
| 3 (Ex. 2) | —NHCH₂CH₃ | Cl |
| 4 (Ex. 2) | —NHCH₂CH₂CH₃ | Cl |
| 5 (Ex. 2) | —NHCH₂CH₂OH | Cl |
| 6 (Ex. 2) | —N(CH₂CH₃)₂ | Cl |
| 7 (Ex. 3) | —OCH₃ | Cl |
| 8 (Ex. 4) | —OCH₃ | OCH₃ |

TABLE 11

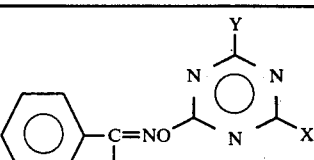

| Compound No. | X | Y |
|---|---|---|
| 9 (Ex. 5) | Cl | Cl |
| 10 (Ex. 6) | NHCH₂CH₃ | Cl |
| 11 (Ex. 6) | NHCH₂CH₂CH₃ | Cl |
| 12 (Ex. 6) | NHCH₂CH₂OH | Cl |
| 13 (Ex. 6) | N(CH₂CH₃)₂ | Cl |

EXAMPLE 1

This example illustrates the preparation of aliphatic amidoxime compounds according to the invention and in particular the preparation of acetamide-O-(4,6-dichloro 1,3,5-triazin-2-yl) oxime having the formula:

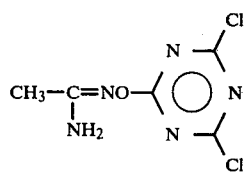

To 2 gr of acetamidoxime dissolved in 60 ml acetone, 2.8 gr NaHCO₃ were added and the mixture was stirred for 15 minutes. The mixture is cooled to 2° C. and a precooled solution of 5 gr cyanuryl chloride in 80 ml acetone and 4.5 ml H₂O were added. Stirring is further continued at 2° C. for 3 hours. The inorganic salts were filtered out and the solvent was evaporated under vacuum. The remaining white solid was crystallized from methylene chloride/hexane to give white crystals which decomp. at 117°–119° C., which have spectoral data confirming the above given formula.

EXAMPLE 2

This example illustrates the preparation of compounds according to the invention and in particular the preparation of acetamide -O-(6-chloro-4-methylamino1,3,5-triazin-2-yl) oxime having the formula:

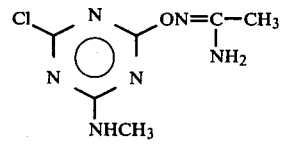

To a stirred solution of 2-methyl amino -4,6-dichloro-1,3,5-triazine (1 gr) in acetone (30 ml), was added a solution of acetamidoxime (0.62 gr) in Acetone (15 ml) and 0.7 gr NaHCO₃ at room temperature. When the addition was complete, stirring was continued for an hour. The mixture was then filtered and the solvent was evaporated under vacuum. The remaining white solid was separated with column chromatography and a white product was isolated, mp - 175° C., which gives one point on the T.L.C. and spectral data confirming the formula given above.

Following the above method, compounds 3,4,5, and 6 of Table 1 were prepared, using the appropriate substituted triazine.

EXAMPLE 3

This example illustrates the preparation of acetamide-O-(6-chloro-4-methoxy-1,3,5-triazin-2-yl) oxime having the formula:

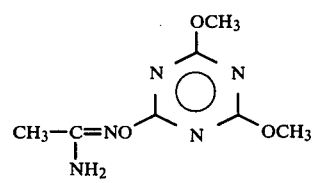

To a stirred solution of 2-methoxy-4,6-dichloro-1,3,5-triazine (1 gr) in acetone (30 ml), was added a solution of acetamidoxime (0.41 gr) in Acetone (10 ml) and 0.47 gr NaHCO₃ at room temperature and stirring was continued for 1 hour. The mixture was then filtered and the solvent was evaporated under vacuum.

The remaining solid was separated with column chromatography on a silica gel with ethyl acetate as eluent. A white solid separated out mp - 132° C., which gives one point on the T.L.C. and spectral data which confirms the formula given above.

EXAMPLE 4

This example illustrates the preparation of derivatives of the compounds according to the invention and in particular the preparation of acetamide-O-(4,6-dimethoxy-1,3,5-triazin-2-yl) oxime, having the formula:

To a stirred solution of 1 gr acetamide-O-(4,6-dichloro-1,3,5-triazine-2-yl) oxime in 50 ml methanol, was added 0.8 gr NaHCO₃ and 6.5 ml H₂O. The mixture is refluxed for 40 minutes. The solvent is evaporated and the reaction was separated on a silica column with ethyl acetate as eluent. A white solid separates, which gives one spot on the T.L.C. and spectral data which confirms the formula given above. mp - 189°-192° C.

EXAMPLE 5

This example illustrates the preparation of aromatic compounds according to the invention, and in particular the preparation of benzamide-O-(4,6 dichloro 1,3,5 triazin -2-yl) oxime, having the formula:

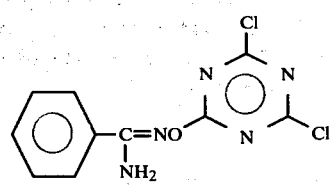

To a stirred solution of 3 gr 2,4,6-trichloro 1,3,5 triazine in acetone (20 ml) at 0°-5° C., was added a pre-cooled (0°-5° C.) solution of 1 gr benzamidoxime in acetone (10 ml) and 1 gr of NaHCO₃. When the addition was complete, stirring was continued for a further 4 hours at about 2° C. The mixture was then filtered and the solvent was evaporated under vacuum. The remaining white solid was crystallized from benzene to give white crystals of mp 157°-159° C., which gave spectral data confirming the formula given above.

EXAMPLE 6

This example illustrates the preparation of aromatic compounds according to the invention and in particular the preparation of benzamide -O-(4-propylamino-6-chloro-1,3,5-triazin-2-yl) oxime, having the formula:

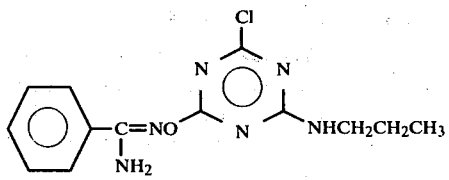

To a stirred solution of 2-n-propylamino-4,6-dichloro-1,3,5-triazine (1 gr) in acetone (30 ml), was added a solution of benzamidoxime (0.66 gr) in acetone (10 ml) and 0.42 gr NaHCO₃ at room temperature. When the addition was complete, stirring was continued for a further 4 hours. The mixture was then filtered and the solvent was evaporated under vacuum. The remaining solid was separated with column chromatography on silica gel with chloroform and 20% ethyl acetate as eluent. A white solid product separates out, which gives one spot on the T.L.C. and has spectra data confirming the above given formula. mp - 146° C. Following the above method, compounds 10, 12 and 13 of Table 11 were prepared using the appropriate substituted triazine.

EXAMPLE 7

This example illustrates the preparation of compounds according to the invention and in particular the preparation of acetamide-O-(6-chloro-4 -ethyl thio-triazin-2-yl) oxime, having the formula:

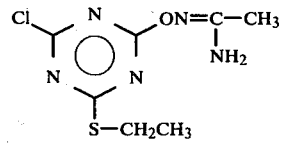

To a stirred solution of 2-ethyl thio-4,6-dichloro 1,3,5-triazine (1 gr) in acetone (30 ml), was added a solution of acetamidoxime (0.35 gr) in acetone (10 ml) and 0.4 gr NaHCO₃. The mixture is stirred for 2 hours at room temperature and then the anorganic salt is filtered out. The solvent is evaporated under vacuum and the remaining solid is separated on a silica gel compound with chloroform as eluent. A solid is obtained, which given one spot in the T.L.C. and has spectroscopic data which confirms the above given formula.

EXAMPLE 8

This example illustrates the preparation of compounds according to the invention and in particular the preparation of acetamide-O-(2,5,6 trichloro pyrimidin 4-yl) oxime, having the formula:

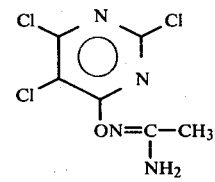

To a stirred solution of 2,4,5,6 tetra chloro pyrimidine in Acetone (50 ml), was added acetamidoxime (0.68 gr) in 15 ml Acetone and a solution of 0.972 gr Na₂CO₃ in 15 ml H₂O at room temperature. The temperature raises in about 5° C. and stirring was continued for another hour. The reaction mixture was poured to cold water and to the precipitate obtained, a column chromatography on silica gel with ethylacetate as eluent was carried out. A solid separates out, which gives one spot on the T.L.C. and has spectral data confirming the above given formula. mp - 157°-158° C.

EXAMPLE 9

This example illustrates the preparation of compounds according to the invention and in particular the preparation of benzamide-O-(2,5,6 trichloro pyrimidin-4-yl) oxime, having the formula:

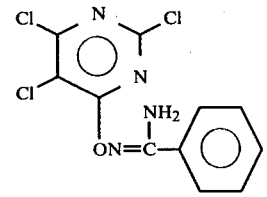

To a stirred solution of 2,4,5,6 tetrachloro pyrimidine (2 gr) in acetone (40 ml) was added a solution of benzamidoxime (1 gr) in Acetone (20 ml) and a solution of 0.43 gr NaOH in 15 ml H₂O at room temperature. When the addition was complete, stirring was continued for a further 2 hours at room temperature. The cloudy mixture was poured then to cold water and the precipitate was filtered to give a solid product with mp - 180°-182° C. and with spectral data confirming the above given formula.

EXAMPLE 10

This example illustrates the preparation of compounds according to the invention and in particular the preparation of the condensation product of acetamidoxime and 2,3-dichloro-quinoxaline, having the formula:

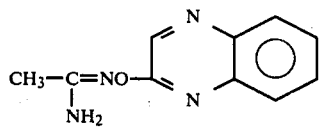

To a stirred solution of 2,3-dichloro-quinoxaline (2 gr) in acetone (60 ml), were added a solution of acetamidoxime (0.74 gr) in acetone (20 ml) and a solution of 1.065 gr Na$_2$CO$_3$ in 15 ml H$_2$O. The solution becomes cloudy and warms up. After 1 hour of stirring at room temperature, the mixture is poured to cold water and the precipitate is filtered out. mp - 198°-9° having spectral data which confirms the above given formula.

Example 11

This example illustrates the preparation of aromatic amidoxime compounds according to the invention and in particular the preparation of the condensation product of benzamidoxime and 2,3 dichloro-quinoxaline, having the formula:

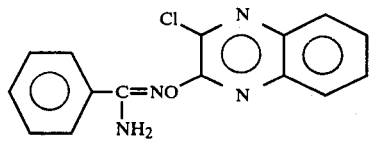

To a stirred solution of 2,3 dichloro-quinoxaline (1.5 gr) in acetone (60 ml) at room temperature, was added a solution of benzamidoxime (1 gr) in acetone (20 ml) and 0.3 gr of NaOH in 5 ml H$_2$O. The temperature was raised to 50° C. and stirring was continued at this temperature for a further 3 hours. After cooling to room temperature, the inorganic salt was filtered out and the solvent was evaporated under vacuum. The remaining solid was seperated on a silica gel column to give a product with mo — 183°-186° C. and spectral data confirming the above given formula.

Example 12

This example illustrates the preparation of compounds according to the invention and in particular the preparation of acetamide-0-(4-ethylamino-2,5-dichloro-pyrimidin-6-yl)oxime, having the formula:

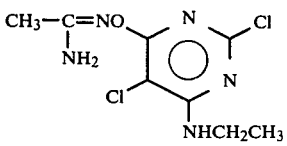

To a stirred solution of 4-ethylamino 2,5,6 trichloro pyrimidine (1 gr) in acetone 30 ml, was added a solution of 0.330 gr acetamidoxime in 20 ml acetone and 0.371 gr NaHCO$_3$. The mixture is stirred for 2 hours at 60° C.

The anorganic salt is filtered out and the solvent is evaporated under vacuum. The remaining solid is seperated on a silica gel column with ethyl acetate as eluent. A white product is obtained with spectral data confirming the above given formula.

Example 13

This example illustrates the preparation of compounds according to the invention and in particular the preparation of the condensation product of succinimidoxime with 2-ethylamino -4,6-dichloro-1,3,5 triazine, having the formula:

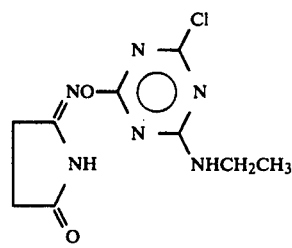

To a stirred solution of 2-ethylamino-4,6-dichloro-1,3,5 triazine (1 gr) in acetone (30 ml), was added a solution of succinimidoxime (0.59 gr) in acetone (20 ml) and 0.435 gr NaHCO$_3$. When addition was complete, stirring was continued for a further 3 hours at room temperature. The mixture was filtered and the solvent was evaporated under vacuum. The remaining solid was separated on a silica gel column with ethyl acetate as eluent. A white product is obtained which has spectral data confirming the above given formula.

Example 14

This example illustrates the preparation of compounds according to the invention and in particular the preparation of the condensation product of malonamidoxime and 2-ethylamino-4,6-dichloro-1,3,5-triazine, having the formula:

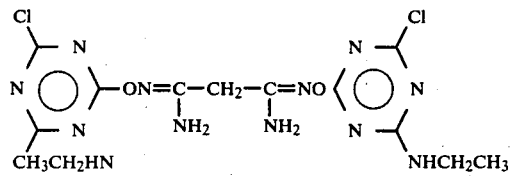

To a stirred solution of malon-amidoxime (0.5 gr) in acetone/H$_2$O mixture (30 m/10 ml), was added a solution of a 4-fold excess 2-ethylamino- 4,6-dichloro-1,3,5-triazine in acetone (30 ml) and 0.64 gr NaHCO$_3$. The mixture was stirred for 3 hours and then filtered. The solvent evaporated under vacuum and the remaining solid was separated on silica gel column with ethyl acetate as eluent. The isolaed product have spectral data confirming the above given formula.

Example 15

Example 14 was repeated using 1,4 benzdiamidoxime and 2-ethylamino-4,6-dichloro-1,3,5-triazine, obtaining a product having the formula:

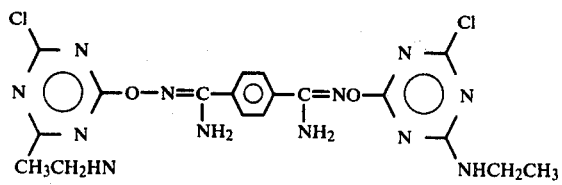

Example 16

10 grms of fibers of polyacrylonitrile vinylacetate (93:7) are placed in a bath containing 10% NH₂OH-HCl and 7.5% Na₂CO₃ at 55° C., and kept for 5 minutes. The fibers are removed washed with water for 10 minutes and placed in a 2% solution of cyanuric chloride at pH 7.0 and 0° C. The fibers are removed after 15 minutes and washed in ice water. The treated fibers are insoluble in NMP, DMF, DMSO, dioxane, ethanol, HCl (conc.) and NaOH (1 M), indicating crosslinking. Elemental analysis and titration indicate the presence of unreacted chloro groups (0.5 meq/gr dry basis) available for further reaction. Thermal gravitimetric analysis indicates a greater thermal stability than the unmodified material, up to 300° C.

Example 17

Example 16 is repeated using particles of polyacrylonitrile 5μ in diameters with a porosity of 60%. The cyanuric chloride step is carried out in pure acetone. The resultant particles have 1.5 meq/gr dry basis of reactive chloro.

EXAMPLE 18

Example 16 is performed with porous fibers (50% porosity) with 1.2 meq/gr chloro groups introduced.

EXAMPLE 19

Examples 16 and 17 are repeated, but after the cyanuric chloride step the fibers are placed in an aqueous polyethylenimine solution (5%) for 10 minutes at a pH of 10. After washing for 2 hours, elemental analysis indicated a bound PEI layer and the fibrous and particles were hydrophilic, but insoluble in common solvents listed in Example 16.

EXAMPLE 20

Example 19 is repeated using polyvinyl alcohol instead of polyethyleneimine, with similar results.

EXAMPLE 21

Example 16, 17 and 19 are repeated using tetrachloropyrimidine instead of cyanuric chloride, where in the reaction with amidoxime derivative is carried out at room temperature and the subsequent reaction with the water soluble polymer at 40° C., with similar results.

EXAMPLE 22

Example 16 is repeated using 2,4,6 trifluoro-5-chloropyrimidine instead of cyanuric chloride. The fiber are crosslinked and elemental analysis and titration indicated 0.55 meq/gr additional reactive groups for further reactions.

EXAMPLE 23

Example 16 and 18 are repeated using a reactive dye formula 1 instead of cyanuric chloride. The fibers were thus dyed. Fibers were similarily dyed with reactive dye formulas 2–5.

Reactive Dye Formulas.

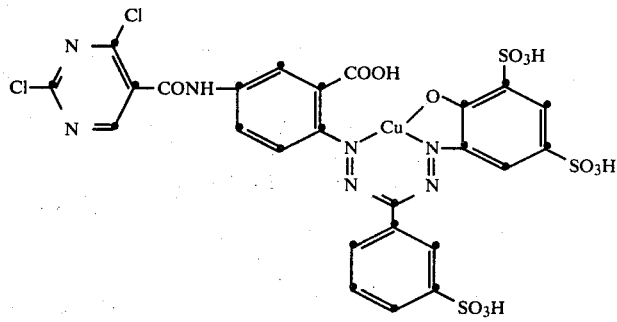

(1)

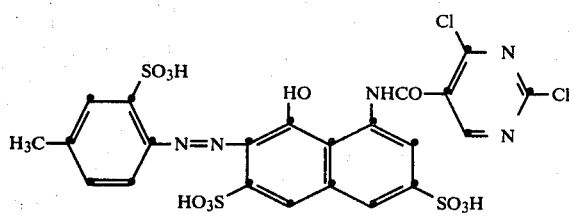

(2)

Reactive Dye Formulas.

-continued

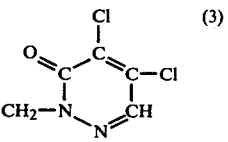

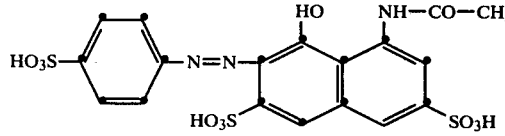 (3)

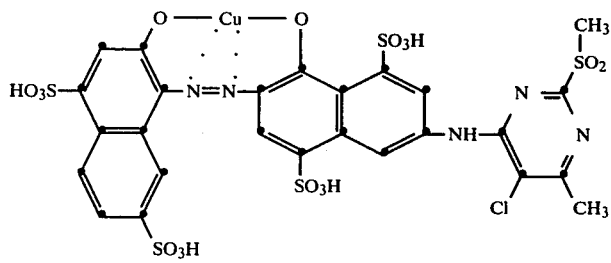 (4)

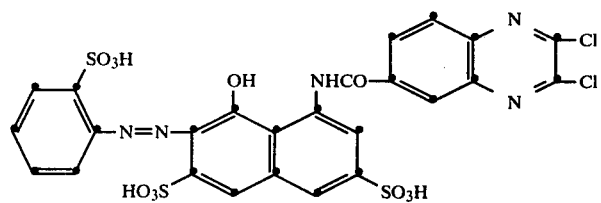 (5)

EXAMPLE 24

Example 16 is repeated using:

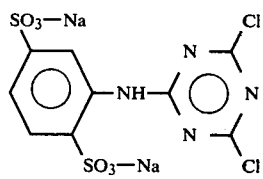

giving fibers with 0.21 meq CL/gr dry weight, and bound sulfonic groups.

EXAMPLE 25

Particles (200–800μ in diameter) with a porosity of 67% were made by a method similar to that described in U.S. Pat. No. 3,639,306, using a copolymer of polyacrylonitrile-vinyl acetate (93/7). Amidoxime functions were then introduced by placing 2 grams of particles in 500 ml of a 10% NH$_2$OH.HCl solution adjusted to pH 6.5 and heated at 55° C. for 20 minutes. The amidoxime particles are then washed with water for 15 minutes and placed in a 2% cyanuryl chloride solution of 4/1 acetone/water solution containing 1% Na$_2$HCO$_3$ at 0°–5° C. for 15 minutes. After washing for 15 minutes in acetone at 0° C., the particles were found to contain by chloro titration (using an American Instrument chloride titrator, Silver Spring, Md., USA) 2.1 meq CL/gr of dried particles.

EXAMPLE 26

Example 25 was repeated, but instead of cyanuric chloride 8 grams of 2 ethylamine, 4,6 dichloro triazine was placed in a solvent mixture of acetone (100 ml), water (100 ml) and dioxane (25 ml) and brought to pH 7–8 with a 15% solution of Na$_2$CO$_3$. The wet amidoxime particles, prepared as in Example 25, were added to this solution with stirring for 20 minutes and the pH was maintained between 7–8 by the addition of 15% Na$_2$CO$_3$. The particles after being filtered and washed thoroughly with dioxane and water had a chloro content of 1.56 meq/gr.

300 mg of the above particles were added to a solution of 60 mg chymotrypsin A$_4$ (C Chymotrypsin) in 3 ml Borax buffer solution at pH 8.5 and room temperature, and left to stand for 24 hours, washed with water, phosphate buffer (pH 7.5) and lyophilised. The activity of the chymotrypsin bound particles was determined using N-succinyl-L-phenylalanine-p-nitroanilide at 25° C. as the substrate and measuring the rate of hydrolysis to p-nitranilin and succinyl-L-phenylalanin at 450 nm. The specific activity (micromoles per minute/gr) was 0.52 U/gr of lyophilized bound enzyme.

EXAMPLE 27

Example 16 is repeated and incubated for 24 hours with whole yeast cells. After washing whole yeast cells were found to be bound to the fibers.

EXAMPLE 28

Example 19 is repeated with microspheres 4μ in diameter. The coated PEI layer is reacted with glutaraldehyde and then with the lectin concanavilin A in the presence of the protector molecule mannose. The particles covered with lectin were packed in a column and were found to adsorb yeast cells and yeast cell fragments.

EXAMPLE 29

1,6 gr of polyacrylonitrile knitted fabric Dralon ® (Bayer) was boiled for 5 minutes in a 10% hydroxyl amine solution at pH 6.5. After washing in water the cloth was dipped for 20 minutes in a 5% acetone solution of cyanuryl chloride at 4° C. containing 1 gr of NaHCO₃ washed with acetone and dipped again in an enzyme solution containing 15 mg α-amylase in 10 cc of 0.05μ phosphate buffer pH 7.0 at 4° C. overnight, washed and dried.

The activity of the preparation was measured by dipping the enzyme bound cloth (1.6 gr) in a 100 ml solution of 2% Dextrin, 0.02μ phosphate buffer pH 6.9 at room temperature. Analysis for maltose formation has been carried out by using Di-nitro salycilic acid. After one hour the conversion to maltose is 280 mg/100 ml solution.

EXAMPLE 30

A fabric made of porous polyacrylonitrile (porosity 40%) from monofilaments with a plain weave and an aperture of 10μ is modified as in Example 29. The resultant fabric was found to convert Dextrin to maltose when immersed in a Dextrin solution or when a starch solution was passed slowly thorugh a depth filter made from the modified fabric.

EXAMPLE 31

This example illustrates the preparation of polymeric material according to the invention and in particular the preparation of polycondensate of 1,4-benzdiamidoxime and 2-ethylamine, 4,6-dichloro-s-triazine of the formula

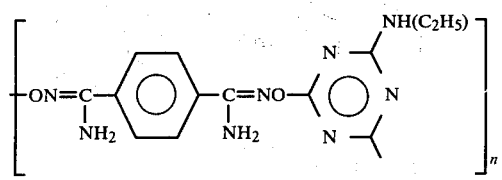

1 gr of benzdiamidoxime and 0.84 NaHCO₃ are suspended in 50 ml acetone. To the stirring mixture a solution of 0.92 gr 2,4,6-trichloro-s-triazine in 20 ml acetone is added. Stirring is continued in room temperature for a further 5 hours. The solid is filtrated and washed with water and acetone.

EXAMPLE 32

This example illustrates the dyeing and finishing process on modified polyacrylonitrile fabrics and fibers and in particular the dyeing of polyacrylonitrile fabric with reactive dyes of formula

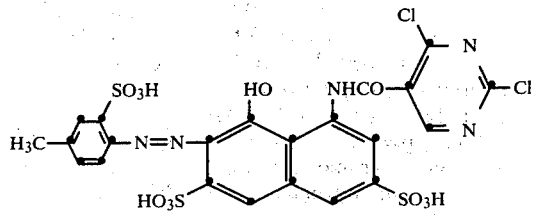

-continued

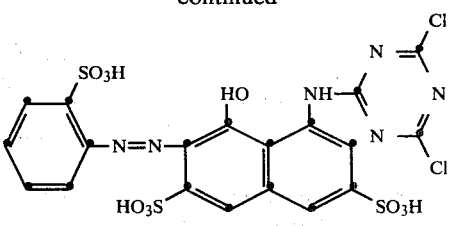

Two pieces of 1 gr Acrilan fabrics were boiled in a 400 ml water solution of 5% hydroxylamine hydrochloride and 5% Na₂CO₃ for 15 minutes. The samples was thoroughly washed with water and then rinsed for 1 hour in a 0.5% dye solution with 2% Na₂CO₃ at a temperature of 32° C. with shaking. The dyed fabrics were thoroughly washed and dried.

Blank dyeing experiments on untreated PAN fabrics, resulted in obtaining undyed fabrics.

It will be evident to those skilled in the art that the invention is not limited to the details of the foregoing illustrative embodiments and that the present invention may be embodied in other specific forms without departing from the essential attributes thereof, and it is, therefore, desired that the present embodiments and examples be considered in all respects as illustrative and not restrictive, reference being made to the appended claims, rather than to the foregoing description, and all changes which come with the meaning and range of equivalency of the claims are, therefore, intended to be embraced therein.

What is claimed is:

1. Compounds of the formula I

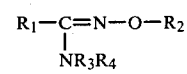

wherein $R_1$ is H, an alkyl group of 1 to 8 carbon atoms, phenyl, a heterocyclic ring structure of 5 to 8 atoms containing one or more nitrogen or oxygen atoms or combinations thereof or a bicyclic condensed ring system optionally containing at least one heterocyclic ring as defined, which groups are optionally substituted by one or more halogen, amine, alkylamine, dialkylamine, amidoxime substituted alkylamine, hydroxy, alkoxy, nitroxide, branched and straight chain alkyl, nitro, cyano, carboxamide, carbonyl, carboxyl, sulphonamide, sulphonimide, phosphonyl, sulphonyl, oxime, amidoxime optionally substituted with a mono or bicyclic heterocyclic radical containing at least two nitrogen atoms which radical itself it optionally substituted by halogen groups; a polymeric radical of the structure

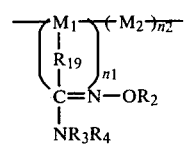

wherein $R_{19}$ is attached to the carbon atom of formula 1 and is a valence bond, an alkyl group of 1 to 4 carbon atoms, a group of the formula $-O-(CH_2)_p$ or $-NH-(CH_2)_p$ where p is 1–6, or

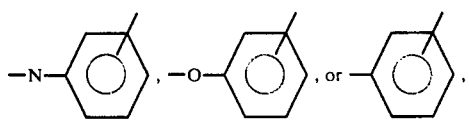

$n_2$ is 0 or a whole number defined by the polymers molecular weight and its relationship to $n_1$ defined by the ratio of $n_2$ to $n_1$, which may take values from 0 to 20, the $n_1$s and $n_2$s are randomly distributed or distributed in blocks in the polymer backbone and $M_1$ and $M_2$ are olefins, wherein $M_2$ may be the same or different monomers such that $M_1$ and $M_2$ form co-, ter-, tetra- or pentapolymers or $M_1$ and $M_2$ are cellulosic or polysaccharides or $M_1$ and $M_2$ are polysulfones, polyphenyleneoxides, polyamides, or epoxy polymers, respectively, wherein the polymer molecular weight may vary from 200–5,000,000 or to such a molecular weight, considered infinite, as may be defined by a crosslinked solid or gel; $R_2$ is a mono or bicyclic heterocyclic radical of cyclic carbonic acid imide derivatives containing at least two nitrogen atoms, and optionally substituted alone or in combination with radicals of halogens, —$NH_2$, mono and dialkyl amino of 1 to 6 carbons per alkyl chain, anilino, napthylamino, —OH, alkoxyl of 1 to 6 carbons, aryloxy; coloured and non-coloured tertiary amines, hydroxy, alkyl ammoniums of 1 to 6 carbons per alkyl chain, sulfonium, phosphonium and carboxylic, sulfonic and phosphonic acid derivatives of mono and dialkyl amino, anilino, naphthylamino, alkoxyl and aryloxy radicals; —SH, alkylthio of 1 to 6 carbon atoms, arylthio, hydrazine, —CN, phosphonic esters, —$SO_2HN_2$, arylsulfonamides, —$SO_3H$, phenyl,alkyl (1 to 6 carbons); synthetic or biological oligomers and polymers, which are substituted in $R_2$ through amino (alkyl or aryl) groups, hydroxyl (alkyl or aryl), sulfhydryl groups or heterocyclic

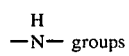

on the synthetic or biological oligomer or polymers, which $R_2$ groups themselves attached to an amidoxime on the same or different amidoxime polymers through $R_{19}$; amidoxime and diamidoxime groups which amidoxime groups themselves optionally are substituted by the hereinbefore defined substituents of $R_1$ and said diamidoxime groups are themselves optionally linked to a further $R_2$ group as hereinbefore defined forming an alternating polymeric structure of diamidoxime and $R_2$ groups; $R_3$ and $R_4$ independently H, or an alkyl of 1 to 4 carbon atoms or one, but not both, is

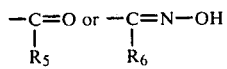

and the other, H, wherein $R_5$ or $R_6$ are alkyls of 2 to 5 carbon atoms optionally substituted by $R_1$, or a phenyl optionally substituted by $R_1$, or $R_6$ and $R_1$ together form structures of the formula

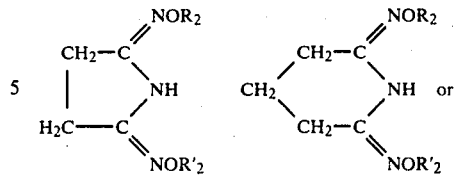

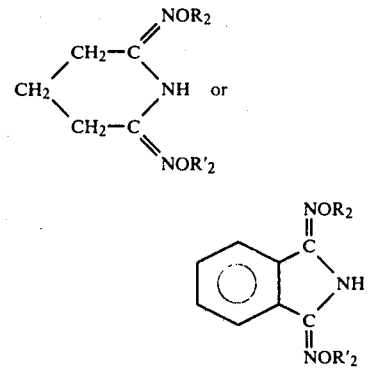

wherein $R_2$ is as defined and wherein $R_2'$ is either $R_2$ or H, or wherein $R_2$ is H and $R_4$ is

and $R_5$ and $R_1$ together form structures of the formula:

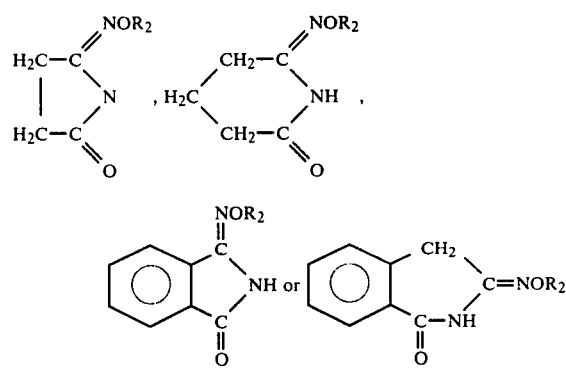

wherein $R_2$ is as defined.

2. Compounds according to claim 1, wherein $R_1$ is an alkyl of 1 to 8 carbon atoms or a phenyl optionally substituted with halogens, or lower alkyls, and $R_3$ and $R_4$ are —H.

3. Compounds according to claim 1, wherein $R_2$ is a cyclic carbonic acid imide radical of a six membered ring containing at least two nitrogen atoms.

4. Compounds according to claim 1, wherein $R_2$ is a cyclic carbonic acid imide bicyclic condensed ring system containing at least one six membered ring of at least two nitrogen atoms.

5. Compounds according to claim 4, wherein $R_2$ is a halogen substituted quinoxaline.

6. Compounds according to claim 1, wherein $R_2$ is a 1,3,5-, 1,2,3- or 1,2,4-triazinyl, pyridazinyl, pyrimidyl, pyrazinyl, pyridazonyl, quinoxalinyl, phthalazinyl or quinazolinyl radical, optionally substituted with halogens, amino, —$NHR_7$, $NR_7R_8$ or —COOH, —CN, —$CONH_2$, $SO_2NH_2$, —$OR_{10}$, or $SR_{11}$ anilino groups, wherein $R_7$, $R_8$, $R_{10}$ and $R_{11}$ are independently H or alkyl chains with 1 to 8 carbons.

7. Compounds according to claim 6, wherein $R_2$ is a triazinyl or pyrimidal substituted by at least one halogen and optionally by an amino, —$NHR_7$,—$NR_7R_8$, anilino group.

8. Compounds according to claim 6, wherein $R_2$ is a triazinyl or pyrimidyl substituted by at least one halogen and optionally by a $-OR_{10}$ or $-SR_{11}$ group.

9. Compounds according to claim 3, wherein $R_2$ is a triazinyl or pyrimidal radical optionally substituted by at least one group selected from halogen, amines, alkylamines, arylamines, dialkylamines, quaternary ammonium, alkoxy and alkylthiol alkyl, carboxyl, cyano, carboxamide and sulfonamide groups.

10. Compounds according to claim 1, wherein the halogen atoms are F, Cl or Br.

11. Compounds according to claim 1, wherein $R_2$ is a 1,3,5-triazinyl or a pyrimidyl substituted by an additional amidoxime radical of the formula IV

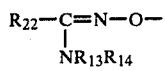

wherein $R_{22}$ independently has one of the values of $R_1$ and $R_{13}$ and $R_{14}$ are independently H or an alkyl of 1 to 4 carbon atoms.

12. Compounds according to claim 1, wherein $R_1$ is substituted with another radical of the formula V

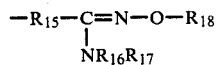

wherein $R_{15}$ independently has one of the values of $R_1$, $R_{16}$ and $R_{17}$ are independently H or an alkyl of 1 to 4 carbon atoms and $R_{18}$ independently has one of the values of $R_2$.

13. Polymeric compounds according to claim 12, wherein $R_2$ and optionally $R_{18}$ is substituted by at least two diamidoxime groups, which groups are themselves linked to further $R_2$ groups forming an alternating polymeric structure of diamidoxime and $R_2$ groups.

14. Polymeric compounds according to claim 13 formed from alternating diamidoxime and triazinyl or pyrimidyl radicals of the formula VI

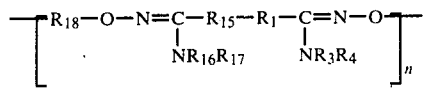

wherein $R_1$, $R_3$, $R_4$, $R_{15}$, $R_{16}$, $R_{17}$, and $R_{18}$ are as defined and n is a whole number of at least 2.

15. Polymeric compounds according to claim 1 of the formula IX

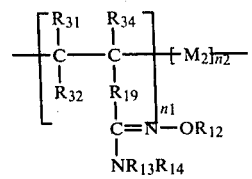

where $R_{34}$ is H or an alkyl radical of 1 to 6 carbons, a phenyl or a halogen and $R_{31}$ and $R_{32}$ are independently radicals of H, halogens or an alkyl of 1 to 6 atoms and $M_2$ is one or more different monomers, which may be chosen individually or in combinations from polymerizable olefinic monomers, and the final molecular weight $n_1+n_2$ may vary from 200 to 5,000,000 or to such a molecular weight considered infinite as defined by a crosslinked substance, and the ratio $n_2/n_1$ varies from 0 to 20, wherein a fraction of the total number of $R_{12}$'s is substituted in part or solely with synthetic or biological oligomers or polymers through the primary or secondary alkylamines, arylamines, hydroxy alkyl, hydroxylaryl or sulfhydryl groups or heterocylic nitrogens of proteins, peptides, lectins, enzymes, hormones, polysaccharides, cellulosics, antibodies, antigens, polynucleotides, whole cells or cellular fragments, polyethylenimine, polyvinyl alcohol, polyvinylimidazole and poly(amino alkyl (meth) acrylates) with alkyls of 1 to 6 carbon atoms.

16. Compounds according to the polymeric structure of claims 1 and 15, wherein $R_{12}$ is substituted with reactive halogens.

17. Polymeric compounds according to claims 15 and 16, wherein M may be chosen from acrylonitrile, vinyl acetate, acrylic acid, methacrylic acid, allyl sulfonate, vinyl alcohol, styrene, allyl halide, or combinations thereof.

18. Compounds according to claims 15 and 16, wherein $M_2$ is acrylonitrile or acrylonitrile and another copolymer is defined, $R_{19}$ is a valence bond, $R_{13}$ and $R_{14}$ are H, and $R_{12}$ is a substituted triazinyl or pyrimidyl radical as defined.

19. Crosslinked compounds according to claims 16, 17 and 18, wherein $R_{12}$ is a triazinyl or pyrimidyl radical substituted with reactive halogens.

20. Crosslinked structures according to claims 15, 16, 17 and 18, wherein $R_{12}$ is substituted in part by biological molecules chosen from enzymes, hormones, peptides, lectins, polysaccharides, proteins, antibodies, antigens, or proteins, and optionally substituted in the same or different $R_{12}$ with the other groups cited in claim 1.

21. Compounds according to claims 15, 17 and 18, wherein $R_2$ is substituted with polyethylimine (PEI) or polyvinyl alcohol (PVA) of a molecular weight between 200 and 200,000 and said PEI or PVA molecule is optionally bound to more than one $R_2$ radical.

22. Crosslinked structures according to claims 15 to 21 in the form of particles, fibers or sheets, all of which are either porous or non-porous.

23. Compounds accorsing to the polymeric structures in claims 1 and 15, wherein $R_{12}$ is a radical derived from reactive dyes or colourless radicals derived from carbonic imide halides containing one or more of the following ionic groups-sulfonic and phosphoric; carboxyl (all in the acid or salt form), quaternary ammoniums, phosphonium or sulfoniums.

24. Compounds according to claims 15, 16, 17, 21, and 22, wherein $R_{12}$ is a reactive dye or colourless radical based on triazinyl, pyrimidyl, quinoxaline-6-carbonyl, pyridazonly, propionyl, 1,4-dichloro-phthalazine-6-carbonyl or benzothiazole.

25. Compounds according to claim 1, wherein $R_3$ is H and $R_4$ is

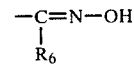

and $R_6$ together with $R_1$ form structures of the formula

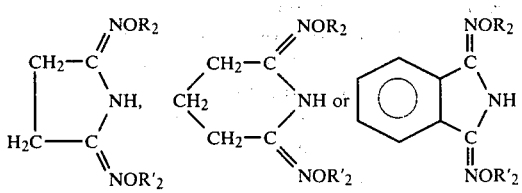

in which $R_2'$ is H or $R_2$.

26. Compounds according to claim 25, wherein $R_2$ is a substituted triazinyl, pyrimidyl or quinoxaline radical as defined.

27. Compounds according to claim 1, wherein $R_3$ is H, $R_4$ is

and $R_5$ together with $R_1$ form structures of the formula

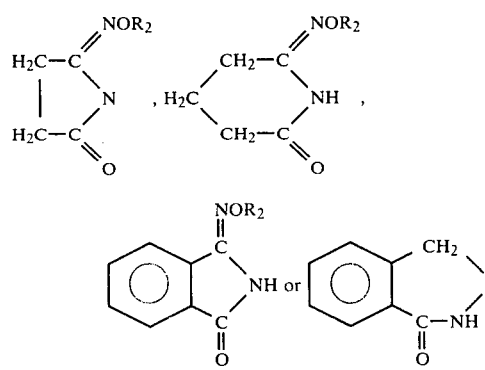

28. Compounds according to claim 27, where $R_2$ is a substituted triazinyl, pyrimidyl or quinoxaline radical as defined.

29. Compounds according to claim 1, having the structure VIII:

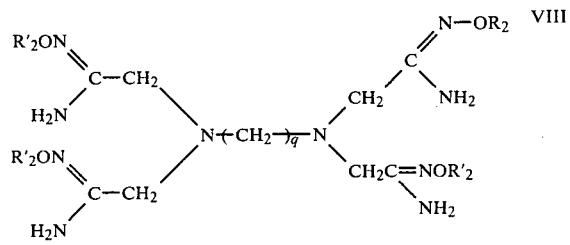

wherein each $R_2'$ is independently either $R_2$ or H, $R_2$ is a triazinyl or pyrimidyl radical and Q is 2, 3 or 6.

30. A process for the manufacture of compounds of claim 1 comprising reacting an amidoxime of the structure:

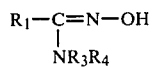

with a compound of the formula $R_2$-Hal, wherein $R_1$, $R_2$, $R_3$ and $R_4$ are as defined in claim 1 to form a compound of the formula I

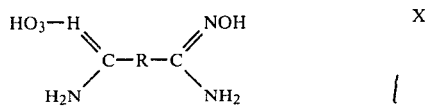

31. A process according to claim 30, wherein $R_2$ is selected from the group consisting of a 1,3,5-, 1,2,3-, 1,2,4-triazinyl, pyridazinyl, pyrimidyl, pyrazinyl, pyridazonyl, quinoxalinyl, phthalazinyl or quinazolinyl radical, optionally substituted with additional halogen, —COOH, —CN, —CONH$_2$, anilino-, —SO$_2$NH$_2$, —NR$_7$R$_8$R$_9$, —OR$_{10}$, or —SR$_{11}$ groups, wherein $R_7$, $R_8$, $R_{10}$ and $R_{11}$ are independently H or alkyl chains with 1 to 8 carbons.

32. A process according to claim 30, wherein $R_2$-Hal is cyanuric chloride, tetrachloropyrimidine or a mono- or di- substituted derivative thereof, wherein said substitutents are selected from the group consisting of amine, hydroxy, alkylamines, hydroxy alkylamines, alkoxy or alkylthiol groups, wherein said alkyl groups contains 1 to 4 carbon atoms.

33. A process according to claim 30 comprising reacting a diamidoxime of the formula X $$HO_3-H\diagdown\phantom{C}\diagup NOH \phantom{xxx} X$$
$$\phantom{xxx}C-R-C$$
$$H_2N\diagup\phantom{C}\diagdown NH_2$$

with a compound of the formula $R_2$-Hal, wherein R is a phenyl group optionally substituted by at least one halogen group, or a radical of the formula $-\!(CH_2\!)_n\!-$ and n=1 or 8.

34. A process for manufacturing a polymeric compound as defined in claim 14 comprising reacting a diamidoxime with a compound of the formula $R_2$-Hal, wherein $R_2$-Hal contains at least two reactive halogen group.

35. A process according to claim 34, wherein $R_2$-Hal is cyanuric chloride or tetrachloropyrimidine.

36. A process for manufacturing a polymeric compound as defined in claims 1 and 15 comprising reacting a polymer containing nitrile groups with a hydroxylamine and then subsequently reacting the product thereof with $R_2$-Hal.

37. A process according to claim 36, wherein $R_2$-Hal is cyanuric chloride or tetrachloropyrimidine, or a substituted $R_2$-Hal of cyanuric chloride or tetrachloropyrimidine, wherein the substituted is a low molecular radical defined in claim 1.

38. A process according to claims 36 and 37, wherein the nitrile containing polymer is polyacrylonitrile or a copolymer of polyacrylonitrile with a vinylacetate, acrylic acid, styrene, methacrylic acid, allyl bromide, acrylic acid or allyl sulfonate.

39. A process according to claims 36, 37 and 38 comprising the further step of reacting a water soluble polymer containing amino or hydroxyl groups with unreacted halogen substituents of the $R_{12}$ radical of compounds of formulas 1a & IX.

40. A process according to claim 39, wherein the water soluble polymer is polyethyleneimine, polyvinyl alcohol, polyvinylamine, or water soluble polysaccharides.

41. A process according to claims 36, 37 and 38 comprising the further step of reacting an enzyme with unreacted halogen substituents of the $R_{12}$ radical of compounds of formulas Ia and IX.

42. A process according to claims 36 and 37 comprising the further step of reacting a lectin, a hormone, an amino acid, a polypeptide, an antibody, an antigen, a whole cell or cellular fragments with unreacted halogen substituents of the $R_2$ radical of compounds of formulas I, Ia and IX.

43. A process according to claims 36 and 37, wherein the $R_2$-Hal compound is reacted with the polyamidoxime polymer under conditions whereby the polymeric material is crosslinked and 0.1 to 3.0 meq of reactive halogen of $R_2$-Hal for each gram of dried polymer or left as substituents of $R_2$ unreacted.

44. A process according to claims 39 through 43, wherein the polymer is in the form of a porous or non-porous particles, fibers, cloth or films.

45. A process according to claims 36, 41 and 42, wherein $R_2$-Hal is a reactive dye based on symmetrical and unsymmetrical triazines and diazines.

46. A process according to claim 44, wherein the original nitrile polymer is in the form of a fiber $1\mu$ to 1 mm in diameter, a fabric or net of such fibers or a particle $0.1\mu$ to 5 mm in diameter, wherein the material is porous or nonporous.

47. A process according to claims 43 through 46, wherein $R_2$-Hal is a reactive dye based on symmetrical and unsymmetrical triazines and diazines and the particle, fiber or fabric is dyed by the process.

48. A process according to claims 43 through 45 comprising the further step of reacting a water soluble polymer containing amino or hydroxyl groups with unreacted halogen substituents of the $R_{12}$ radical of compounds of formula IX, wherein the net, fiber, fabric or particle is made hydrophilic.

49. A process according to claims 43 and 44 comprising the further step of reacting an enzyme with unreacted halogen substituents of the $R_{12}$ radical of compounds of formula Ia and IX.

50. A process according to claims 43 and 44 comprising the further step of reacting a lectin, a hormone, an amino acid, a polypeptide, an antibody, an antigen, a whole cell or cellular fragments with unreacted halogen substituents of the $R_{12}$ radical of compounds of formulas Ia and IX.

51. A process according to claim 48, wherein the product is used in an enzyme reactor.

52. A process according to claim 49, wherein the product is used in an affinity chromatography column.

* * * * *